(12) United States Patent
Stoyanov et al.

(10) Patent No.: US 12,706,223 B2
(45) Date of Patent: Aug. 11, 2026

(54) COMPRESSION OF CATALOGUE OF SURGICAL VIDEO

(71) Applicant: DIGITAL SURGERY LIMITED, London (GB)

(72) Inventors: Danail V. Stoyanov, London (GB); Imanol Luengo Muntion, Bilbao (ES); Petros Giataganas, London (GB); Guathier Camille Louis Gras, London (GB)

(73) Assignee: DIGITAL SURGERY LIMITED, London (GB)

(*) Notice: Subject to any disclaimer, the term of this patent is extended or adjusted under 35 U.S.C. 154(b) by 277 days.

(21) Appl. No.: 18/707,704

(22) PCT Filed: Nov. 10, 2021

(86) PCT No.: PCT/GR2021/000069
§ 371 (c)(1),
(2) Date: May 6, 2024

(87) PCT Pub. No.: WO2023/084258
PCT Pub. Date: May 19, 2023

(65) Prior Publication Data
US 2026/0162834 A1 Jun. 11, 2026

(51) Int. Cl.
*G16H 70/20* (2018.01)

(52) U.S. Cl.
CPC .................................. *G16H 70/20* (2018.01)

(58) Field of Classification Search
CPC ..................................................... G16H 70/20
See application file for complete search history.

(56) References Cited

U.S. PATENT DOCUMENTS

2007/0013776 A1 1/2007 Venetianer et al.
2020/0226757 A1 7/2020 Hare, II et al.
2021/0287785 A1 9/2021 Fabbri et al.
2026/0066102 A1* 3/2026 Corsaro ................ G16H 40/20
2026/0080986 A1* 3/2026 Nadler .................. G16H 10/60
2026/0081005 A1* 3/2026 Nadler .................. G16H 40/20

OTHER PUBLICATIONS

International Search Report and Written Opinion for Application No. PCT/GR2021/000069; International Filing Date: Nov. 10, 2021; Date of Mailing: Sep. 8, 2022; 9 pages.

* cited by examiner

*Primary Examiner* — Y Lee
(74) *Attorney, Agent, or Firm* — CANTOR COLBURN LLP; Robert Crist

(57) ABSTRACT

Data captured during a surgical procedure can include multiple video streams, such as from an endoscopic camera, an external camera, etc., along with data from one or more instruments used during the surgical procedure. Transferring the surgical data over communication networks, and storing the surgical data, is therefore resource-intensive, and a technical challenge. Technical solutions are described to optimize the surgical data by intelligent compression methods that can adaptively reduce the size of certain procedural workflows. In some aspects, the compression reduces the storage/transmission resources required for a video catalogue by reducing redundancy from across the several videos stored in the video catalogue. The compression also enables faster querying and searching through a catalogue or collection of archived data.

20 Claims, 8 Drawing Sheets

COMPRESSION OF CATALOGUE OF SURGICAL VIDEO

CROSS REFERENCE TO RELATED APPLICATIONS

This application is a National Stage application of PCT/GR2021/000069, filed Nov. 10, 2021, which is incorporated by reference in its entirety herein.

BACKGROUND

The present invention relates in general to computing technology and relates more particularly to computing technology for compressing data captured during surgical procedures or a series of procedures based on automatic detection of features in the captured data, such as surgical phases and instruments, using machine learning prediction.

Computer-assisted systems, and particularly computer-assisted surgery systems, rely on video data digitally captured during a surgery. Such video data can be stored and/or streamed or processed during a surgical procedure. In some cases, the video data can be used to augment a person's physical sensing, perception, and reaction capabilities or the capabilities of an instrument. For example, such systems can effectively provide the information corresponding to an expanded field of vision, both temporal and spatial, that enables a person to adjust current and future actions based on the part of an environment not included in his or her physical field of view. Alternatively, or in addition, the video data can be stored and/or transmitted for several purposes such as archival, training, post-surgery analysis, event logging, patient consultation, etc.

SUMMARY

According to one or more aspects, a computer-implemented method includes segmenting, by a processor, a first video of a surgical procedure into a sequence of video portions. The method further includes generating, by the processor, a first sequence of latent representations corresponding to the sequence of video portions in the first video using an encoder machine learning model. The method further includes computing, by the processor, a similarity score of the first video and a second video from a video catalogue that comprises a plurality of videos, including the second video, the computing based on the first sequence of latent representations and a second sequence of latent representations of the second video. The method further includes determining, by the processor, a compression rate for the first video based on the similarity score. The method further includes generating, by the processor, a compressed first video by compressing the first video using the compression rate that is determined. The method further includes storing, by the processor, the compressed first video in the video catalogue.

In one or more aspects, the first video is stored in an archive, and the video catalogue is updated to store a link between the compressed first video and the first video in the archive.

In one or more aspects, the first video is segmented, using one or more machine learning models, into the sequence of video portions, wherein each video portion represents a maneuver in the surgical procedure.

In one or more aspects, the first video is captured using a camera that is one from a group comprising an endoscopic camera, a portable camera, and a stationary camera.

In one or more aspects, the second video is stored using a first compression rate, the first compression rate providing high-fidelity, and based on the similarity score being within a predetermined range, using a second compression rate for the first video, the second compression rate providing a lower fidelity than the second video.

In one or more aspects, the second video is of the same surgical procedure as the first video.

In one or more aspects, the second video is of a different surgical procedure than the first video.

In one or more aspects, the first video and the second video capture respective surgical procedures, and the second video is selected to be compared with the first video based on one or more attributes selected from a group of attributes comprising type of the surgical procedure, institution of the surgical procedure, staff performing the surgical procedure, equipment used for the surgical procedure, patient of the surgical procedure, and camera used to capture the first video.

In one or more aspects, the method further includes, in response to receiving, from a user, a request to playback the first video from the video catalogue, notifying the user of the compressed first video, the first video from the archive, and the second video from the video catalogue.

In one or more aspects, the user can select, for playback, one from the compressed first video, the first video from the archive, and the second video from the video catalogue.

According to one or more aspects, a system includes a machine learning system comprising one or more machine learning models that are trained to encode a portion of video into a latent representation. The system further includes a data collection system configured to generate a compressed copy of a video catalogue that comprises a plurality of videos, each video in the video catalogue comprising a plurality of video portions. Generating the compressed copy of the video catalogue includes generating a first sequence of latent representations corresponding to a first sequence of video portions in a first video using the machine learning system. Generating the compressed copy of the video catalogue further includes computing a plurality of similarity scores of the first video with the plurality of videos from the video catalogue, a similarity score between the first video and a second video from the plurality of videos is computed based on the first sequence of latent representations and a second sequence of latent representations of the second video. Generating the compressed copy of the video catalogue further includes based on a determination that the first video is similar to the second video based on the similarity score, generating a compressed first video using a compression protocol that is based on the similarity score. Generating the compressed copy of the video catalogue further includes storing the compressed first video in the video catalogue.

In one or more aspects, the plurality of similarity scores is stored in metadata of the video catalogue.

In one or more aspects, the plurality of similarity scores is stored in metadata of the compressed first video.

In one or more aspects, the first video is archived, and the compressed first video is linked to the first video that is archived.

In one or more aspects, in response to the similarity score being within a first range that indicates that the first video is similar to the second video, a compression rate is adjusted to a higher value, and in response to the similarity score being within a second range that indicates that the first video is not similar to the second video, the compression rate is adjusted to a lower value.

In one or more aspects, adjusting the compression rate comprises adjusting one or more attributes from a group comprising image size, frame rate, amount of movement between frames, bit rate, and codec.

According to one or more aspects, a computer program product includes a memory device having computer-executable instructions stored thereon, which when executed by one or more processors cause the one or more processors to perform a method to catalogue surgical data in a compressed manner. The method includes generating, using a machine learning system, a latent representation space corresponding to a data collection system that stores surgical data for a plurality of surgical procedures, the latent representation space comprising a plurality of latent representations, wherein a latent representation is a vector representation of a portion of surgical data, and wherein each surgical data in the data collection system comprises a plurality of portions. The method further includes, in response to receiving a first surgical data to be catalogued in the data collection system, segmenting the first surgical data into a sequence of portions. Further, a first sequence of latent representations corresponding to the sequence of portions in the first surgical data is generated using the machine learning system. Further, from the latent representation space, a second surgical data is determined that is similar to the first surgical data by comparing the first sequence of latent representations of the first surgical data and a second sequence of latent representations of the second surgical data. Further, a similarity score of the first surgical data and the second surgical data is computed. A first compression rate is determined by adjusting a second compression rate based on the similarity score, the second compression rate is used to store the second surgical data in the data collection system. Further, a compressed first surgical data is generated using the first compression rate. In one or more aspects, the compressed first surgical data is stored in the data collection system.

In one or more aspects, the first compression rate is higher than the second compression rate.

In one or more aspects, storing the compressed first surgical data in the data collection system comprises storing a link between the compressed first surgical data and the second surgical data.

In one or more aspects, in response to receiving a third surgical data to be catalogued in the data collection system, the third surgical data is segmented into a third sequence of portions. Further, a third sequence of latent representations is generated corresponding to the third sequence of portions in the third surgical data using the machine learning system. Further, based on the latent representation space, it is determined that the third surgical data is not similar to any of the surgical data in the data collection system. The third surgical data is stored in the data collection system using the second compression rate, and the third sequence of latent representations is stored in the latent representation space.

Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

Figure 1:
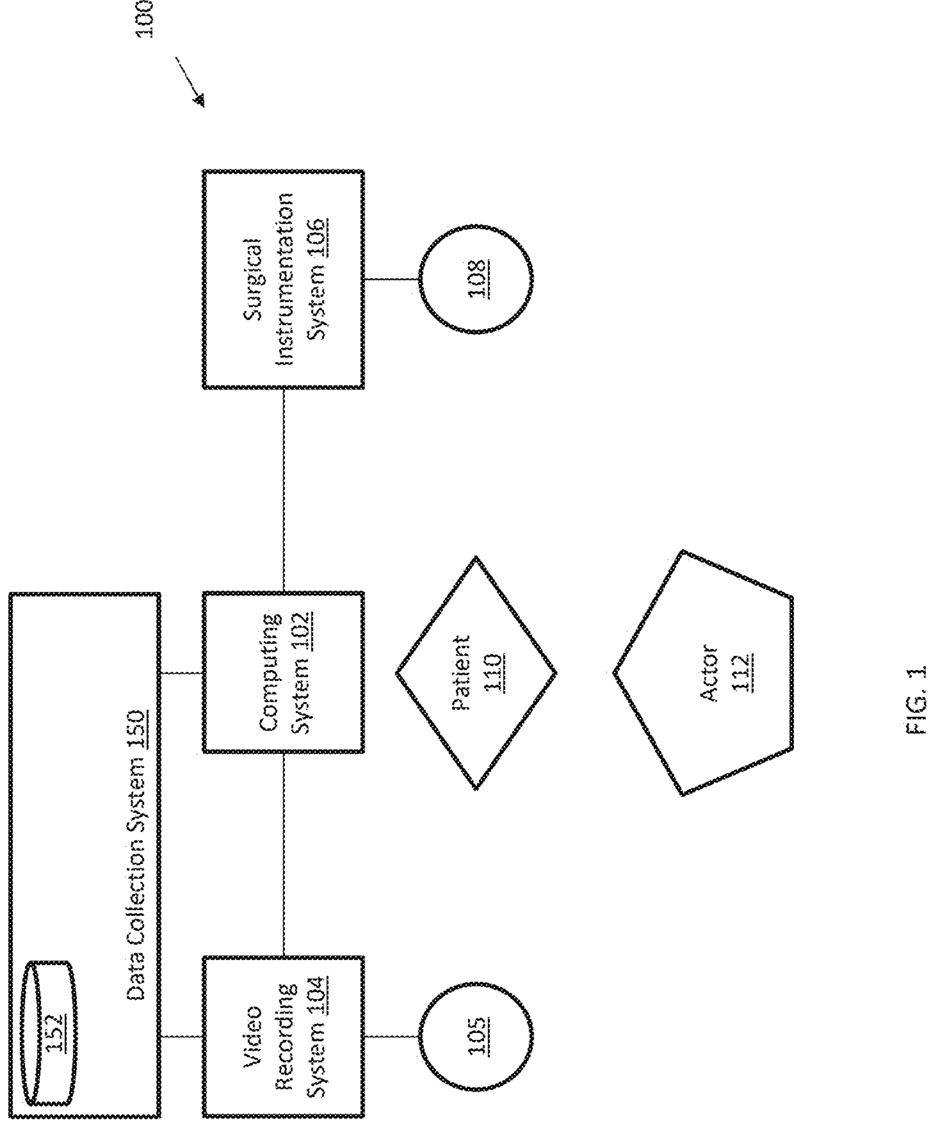
FIG. 1 shows a computer-assisted surgery system according to one or more aspects.

The diagrams depicted herein are illustrative. There can be many variations to the diagram, or the operations described therein without departing from the spirit of the invention. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

In exemplary aspects of the technical solutions described herein, a computer-assisted surgical (CAS) system is provided that uses one or more machine learning models to capture, as surgical data, data that is sensed by an actor involved in performing one or more actions during a surgical procedure (e.g., a surgeon). The surgical data includes one or more surgical videos and associated device information. For example, the device information can include signals collected during surgery (e.g., data from instruments, energy devices, robotic motion controllers, or other imaging sources). Exemplary aspects of the technical solutions described herein improve the CAS system by facilitating automatic removal of redundant data from a catalogue of surgical videos. Exemplary aspects of the technical solutions described herein improve the CAS system by reducing the amount of storage required to store the surgical videos. Alternatively, or in addition, exemplary aspects of the technical solutions described herein improve the CAS system by reducing the network bandwidth required to transmit the surgical videos or to query and search through the whole or a subset of the surgical video catalogue.

The surgical data that is captured can include one of more videos of a surgical procedure ("surgical video"), which may be captured using an endoscopic or microscopic camera passed inside a patient adjacent to the location of the surgical procedure to view and record one or more actions performed during the surgical procedure. A video may also come from a camera mounted in the operating room and external to the surgical site. The video that is captured can be transmitted and/or recorded in one or more examples. In some examples, the video can be analyzed and annotated post-surgery. A technical challenge exists to store the vast amounts of video data generated due to the numerous surgical procedures performed. Exemplary aspects of technical solutions described herein relate to, among other things, devices, systems, methods, computer-readable media, techniques, and methodologies for maintaining video of surgical procedures.

Additionally, exemplary aspects of technical solutions described herein relate to, among other things, devices, systems, methods, computer-readable media, techniques, and methodologies for using machine learning and computer vision to automatically predict or detect surgical phases, anatomical information, and instrument information in surgical data, in order to predict different compression rates for different videos in a video catalogue. More generally, aspects can include object detection, motion tracking, and predictions associated with one or more structures, the structures being deemed to be critical for an actor involved in performing one or more actions during a surgical procedure (e.g., by a surgeon) or to determine the importance of a surgical phase or process. A predicted structure can be an anatomical structure, a surgical instrument, an event, etc. Alternatively, or in addition, the structures are predicted in an offline manner, for example, from stored surgical data.

The surgical data provided to train the machine learning models can include data captured during a surgical procedure and simulated data. The surgical data can include time-varying image data (e.g., a simulated/real video stream from different types of cameras) corresponding to a surgical environment. The surgical data can also include other types of data streams, such as audio, radio frequency identifier (RFID), text, robotic sensors, energy profiles from instruments, other signals, etc. The machine learning models are trained to predict and identify, in the surgical data, "structures," including particular tools, anatomic objects, actions being performed in the simulated/real surgical stages. In one or more aspects, the machine learning models are trained to define one or more models' parameters to learn how to transform new input data (that the models are not trained on) to identify one or more structures. During the training, the models receive, as input, one or more data streams that may be augmented with data indicating the structures in the data streams, such as indicated by metadata and/or image-segmentation data associated with the input data. The data used during training can also include temporal sequences of one or more input data.

In one or more aspects, the simulated data can be generated to include image data (e.g., which can include time-series image data or video data and can be generated in any wavelength of sensitivity) that is associated with variable perspectives, camera poses, lighting (e.g., intensity, hue, etc.) and/or motion of imaged objects (e.g., tools). In some instances, multiple data sets can be generated—each of which corresponds to the same imaged virtual scene but varies with respect to perspective, camera pose, lighting, and/or motion of imaged objects, or varies with respect to the modality used for sensing, e.g., red-green-blue (RGB) images or depth or temperature or specific illumination spectra or contrast information. In some instances, each of the multiple data sets corresponds to a different imaged virtual scene and further varies with respect to perspective, camera pose, lighting, and/or motion of imaged objects.

The machine learning models can include, for instance, a fully convolutional network adaptation (FCN), graph neural network, and/or conditional generative adversarial network model configured with one or more hyperparameters for phase and/or surgical instrument detection. For example, the machine learning models (e.g., the fully convolutional network adaptation) can be configured to perform supervised, self-supervised, or semi-supervised semantic segmentation in multiple classes—each of which corresponding to a particular surgical instrument, anatomical body part (e.g., generally or in a particular state), and/or environment. Alternatively, or in addition, the machine learning model (e.g., the conditional generative adversarial network model) can be configured to perform unsupervised domain adaptation to translate simulated images to semantic instrument segmentations. It is understood that other types of machine learning models or combinations thereof can be used in one or more aspects. Machine learning models can further be trained to perform surgical phase detection and may be developed for a variety of surgical workflows, as further described herein. Machine learning models can be collectively managed as a group, also referred to as an ensemble, where the machine learning models are used together and may share feature spaces between elements of the models. As such, reference to a machine learning model or machine learning models herein may refer to a combination of multiple machine learning models that are used together, such as operating on the same group of data. Although specific examples are described with respect to types of machine learning models, other machine learning and/or deep learning techniques can be used to implement the features described herein.

In one or more aspects, one or more machine learning models are trained using a joint training process to find correlations between multiple tasks that can be observed and predicted based on a shared set of input data. Further machine learning refinements can be achieved by using a portion of a previously trained machine learning network to further label or refine a training dataset used in training the one or more machine learning models. For example, semi-supervised or self-supervised learning can be used to initially train the one or more machine learning models using partially annotated input data as a training dataset. The partially annotated training dataset may be missing labels on some of the data associated with a particular input, such as missing labels on instrument data. An instrument network learned as part of the one or more machine learning models can be applied to the partially annotated training dataset to add missing labels to partially labeled instrument data in the training dataset. The updated training dataset with at least a portion of the missing labels populated can be used to further train the one or more machine learning models. This iterative training process may result in model size compression for faster performance and can improve overall accuracy by training ensembles. Ensemble performance improvement can result where feature sets are shared such that feature sets related to surgical instruments are also used for surgical phase detection, for example. Thus, improving the performance aspects of machine learning related to instrument data may also improve the performance of other networks that are primarily directed to other tasks.

After training, the one or more machine learning models can then be used in real-time to process one or more data streams (e.g., video streams, audio streams, RFID data, etc.). The processing can include predicting and characterizing one or more surgical phases, instruments, and/or other structures within various instantaneous or block time periods.

The structures can be used to identify a stage within a surgical workflow (e.g., as represented via a surgical data structure), predict a future stage within a workflow, the remaining time of the operation, etc. Workflows can be segmented into a hierarchy, such as events, actions, steps, surgical objectives, phases, complications, and deviations from a standard workflow. For example, an event can be camera in, camera out, bleeding, leak test, etc. Actions can include surgical activities being performed, such as incision, grasping, etc. Steps can include lower-level tasks as part of performing an action, such as first stapler firing, second stapler firing, etc. Surgical objectives can define a desired outcome during surgery, such as gastric sleeve creation, gastric pouch creation, etc. Phases can define a state during a surgical procedure, such as preparation, surgery, closure, etc. Complications can define problems, or abnormal situations, such as hemorrhaging, staple dislodging, etc. Deviations can include alternative routes indicative of any type of change from a previously learned workflow. Aspects can include workflow detection and prediction, as further described herein.

FIG. 1 depicts an example CAS system according to one or more aspects. The CAS system 100 includes at least a computing system 102, a video recording system 104, and a surgical instrumentation system 106.

Actor 112 can be medical personnel that uses the CAS system 100 to perform a surgical procedure on a patient 110. Medical personnel can be a surgeon, assistant, nurse, administrator, or any other actor that interacts with the CAS system 100 in a surgical environment. The surgical procedure can be any type of surgery, such as but not limited to cataract surgery, laparoscopic cholecystectomy, endoscopic endonasal transsphenoidal approach (eTSA) to resection of pituitary adenomas, or any other surgical procedure. The surgical procedure, in some cases, may be a robotic surgery, i.e., actor 112 is a robot, for example, a robotic partial nephrectomy, a robotic prostatectomy, etc. In other examples, actor 112 can be a technician, an administrator, an engineer, or any other such personnel that interacts with the CAS system 100. For example, actor 112 can record data from the CAS system 100, configure/update one or more attributes of the CAS system 100, review past performance of the CAS system 100, repair the CAS system 100, etc.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 108 (e.g., forceps) are used to achieve a specific objective by performing one or more surgical actions. As used herein, a "surgical maneuver" can refer to any of a surgical phase, a surgical action, a step, etc.

The surgical instrumentation system 106 provides electrical energy to operate one or more surgical instruments 108 to perform the surgical actions. The electrical energy triggers an activation in the surgical instrument 108. The electrical energy can be provided in the form of an electrical current or an electrical voltage. The activation can cause a surgical action to be performed. The surgical instrumentation system 106 can further include electrical energy sensors, electrical impedance sensors, force sensors, bubble and occlusion sensors, and various other types of sensors. The electrical energy sensors can measure and indicate an amount of electrical energy applied to one or more surgical instruments 108 being used for the surgical procedure. The impedance sensors can indicate an amount of impedance measured by the surgical instruments 108, for example, from the tissue being operated upon. The force sensors can indicate an amount of force being applied by the surgical instruments 108. Measurements from various other sensors, such as position sensors, pressure sensors, flow meters, can also be input.

The video recording system 104 includes one or more cameras, such as operating room cameras, endoscopic cameras, etc. The cameras capture video data of the surgical procedure being performed. The video recording system 104 includes one or more video capture devices that can include cameras placed in the surgical room to capture events surrounding (i.e., outside) the patient being operated upon. The video recording system 104 further includes cameras that are passed inside (e.g., endoscopic cameras) the patient to capture endoscopic data. The endoscopic data provides video and images of the surgical procedure.

The computing system 102 includes one or more memory devices, one or more processors, a user interface device, among other components. The computing system 102 can execute one or more computer-executable instructions. The execution of the instructions facilitates the computing system 102 to perform one or more methods, including those described herein. The computing system 102 can communicate with other computing systems via a wired and/or a wireless network. In one or more examples, the computing system 102 includes one or more trained machine learning models that can detect and/or predict features of/from the surgical procedure that is being performed or has been performed earlier. Features can include structures such as anatomical structures, surgical instruments (108), or other representations of spatial information in the captured video of the surgical procedure. Features can further include events such as phases, actions in the surgical procedure. Features that are detected can further include actor 112, patient 110. Based on the detection, the computing system 102, in one or more examples, can provide recommendations for subsequent actions to be taken by actor 112. Alternatively, or in addition, the computing system 102 can provide one or more reports based on the detections. The detections by the machine learning models can be performed in an autonomous or semi-autonomous manner.

The machine learning models can include artificial neural networks, such as deep neural networks, convolutional neural networks, graph networks, recurrent neural networks, encoders, decoders, or any other type of machine learning model. The machine learning models can be trained in a supervised, unsupervised, or hybrid manner. The machine learning models can be trained to perform detection and/or prediction using one or more types of data acquired by the CAS system 100. For example, the machine learning models can use the video data captured via the video recording system 104. Alternatively, or in addition, the machine learning models use the surgical instrumentation data from the surgical instrumentation system 106. In yet other examples, the machine learning models may use any combination of video data and surgical instrumentation data or other device data captured during the surgical procedure.

Additionally, in some examples, the machine learning models can also use audio data captured during the surgical procedure. The audio data can include sounds emitted by the surgical instrumentation system 106 while activating one or more surgical instruments 108. Alternatively, or in addition, the audio data can include voice commands, snippets, or dialog from one or more actors 112. The audio data can further include sounds made by the surgical instruments 108 during their use.

In one or more examples, the machine learning models can detect surgical actions, surgical phases, anatomical structures, surgical instruments, and various other features from the data associated with a surgical procedure. The detection can be performed in real-time in some examples. Alternatively, or in addition, the computing system 102 analyzes the surgical data, i.e., the various types of data captured during the surgical procedure, in an offline manner (e.g., post-surgery). In one or more examples, the machine learning models detect surgical maneuvers based on detecting some of the features such as the anatomical structure, surgical instruments, etc.

A data collection system 150 can be employed to store the surgical data. In some aspects, "surgical data" of a surgical procedure is a set of all captured data for the surgical procedure synchronized to a captured video of the surgical procedure being performed. The surgical data P={video, video-synchronized data, procedure data}. Here, the video captures the surgical procedure; video-synchronized data includes device data (e.g., energy profiles, surgical instrument activation/deactivation, etc.); and procedure data includes metadata of the surgical procedure (e.g., surgeon identification and demographic information, patient identification and demographic information, hospital identification and demographic information, etc.). The surgical data P can include additional information in some aspects. In some examples, an electronic medical record of the patient can be used to populate the surgical data.

The data collection system 150 includes one or more storage devices 152. The data collection system 150 can be a local storage system, a cloud-based storage system, or a combination thereof. Further, the data collection system 150 can use any type of cloud-based storage architecture, for example, public cloud, private cloud, hybrid cloud, etc. In some examples, the data collection system can use distributed storage, i.e., the storage devices 152 are located at different geographic locations. The storage devices 152 can include any type of electronic data storage media used for recording machine-readable data, such as semiconductor-based, magnetic-based, optical-based storage media, or a combination thereof. For example, the data storage media can include flash-based solid-state drives (SSDs), magnetic-based hard disk drives, magnetic tape, optical discs, etc.

In one or more examples, the data collection system 150 can be part of the video recording system 104, or vice-versa. In some examples, the data collection system 150, the video recording system 104, and the computing system 102, can communicate with each other via a communication network, which can be wired, wireless, or a combination thereof. The communication between the systems can include the transfer of data (e.g., video data, instrumentation data, etc.), data manipulation commands (e.g., browse, copy, paste, move, delete, create, compress, etc.), data manipulation results, etc. In one or more examples, the computing system 102 can manipulate the data already stored/being stored in the data collection system 150 based on outputs from the one or more machine learning models, e.g., phase detection, structure detection, etc. Alternatively, or in addition, the computing system 102 can manipulate the data already stored/being stored in the data collection system 150 based on information from the surgical instrumentation system 106.

In one or more examples, the video captured by the video recording system 104 is stored on the data collection system 150. In some examples, the computing system 102 curates parts of the video data being stored on the data collection system 150. In some examples, the computing system 102 filters the video captured by the video recording system 104 before it is stored on the data collection system 150. Alternatively, or in addition, the computing system 102 filters the video captured by the video recording system 104 after it is stored on the data collection system 150.

Figure 2:
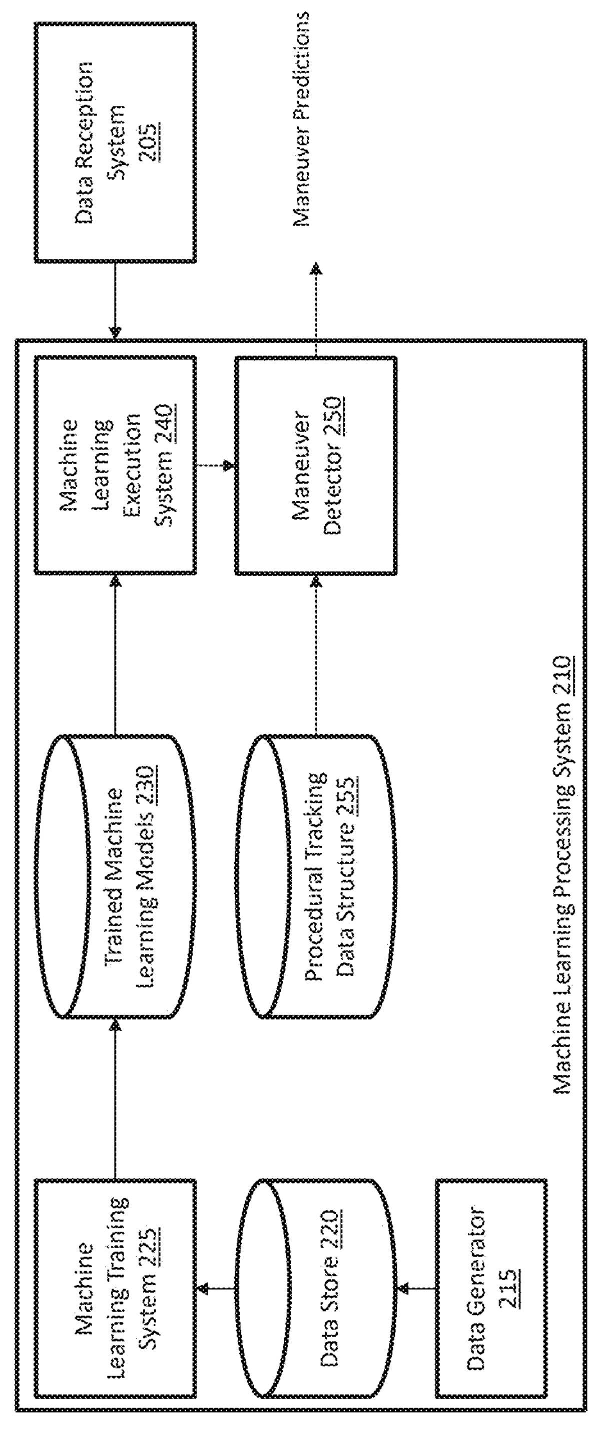
FIG. 2 shows a system for analyzing the video captured by a video recording system according to one or more aspects.

FIG. 2 shows a system 200 for analyzing the video captured by the video recording system according to one or more aspects. The analysis can result in predicting surgical maneuvers and structures (e.g., instruments, anatomical structures, etc.) in the video data using machine learning. The system 200 can be the computing system 102, or a part thereof in one or more examples. System 200 uses data streams in the surgical data to identify procedural states according to some aspects.

System 200 includes a data reception system 205 that collects surgical data, including the video data and surgical instrumentation data. The data reception system 205 can include one or more devices (e.g., one or more user devices and/or servers) located within and/or associated with a surgical operating room and/or control center. The data reception system 205 can receive surgical data in real-time, i.e., as the surgical procedure is being performed. Alternatively, or in addition, the data reception system 205 can receive or access surgical data in an offline manner, for example, by accessing data that is stored in the data collection system 150.

System 200 further includes a machine learning processing system 210 that processes the surgical data using one or more machine learning models to identify one or more features, such as surgical maneuvers, instrument, anatomical structure, etc., in the surgical data. It will be appreciated that machine learning processing system 210 can include one or more devices (e.g., one or more servers), each of which can be configured to include part or all of one or more of the depicted components of the machine learning processing system 210. In some instances, a part or all of the machine learning processing system 210 is in the cloud and/or remote from an operating room and/or physical location corresponding to a part or all of data reception system 205. It will be appreciated that several components of the machine learning processing system 210 are depicted and described herein. However, the components are just one example structure of the machine learning processing system 210, and that in other examples, the machine learning processing system 210 can be structured using a different combination of the components. Such variations in the combination of the components are encompassed by the technical solutions described herein.

The machine learning processing system 210 includes a machine learning training system 225, which can be a separate device (e.g., server) that stores its output as one or more trained machine learning models 230. The machine learning models 230 are accessible by a model execution system 240. The model execution system 240 can be separate from the machine learning training system 225 in some examples. In other words, in some aspects, devices that "train" the models are separate from devices that "infer," i.e., perform real-time processing of surgical data using the trained machine learning models 230.

Machine learning processing system 210, in some examples, further includes a data generator 215 to generate simulated surgical data, such as a set of virtual images, or record the video data from the video recording system 104, to train the machine learning models 230. Data generator 215 can access (read/write) a data store 220 to record data, including multiple images and/or multiple videos. The images and/or videos can include images and/or videos collected during one or more procedures (e.g., one or more surgical procedures). For example, the images and/or video may have been collected by a user device worn by the actor 112 (e.g., surgeon, surgical nurse, anesthesiologist, etc.) during the surgery, a non-wearable imaging device located within an operating room, or an endoscopic camera inserted inside the patient 110. The data store 220 is separate from the data collection system 150 in some examples. In other examples, the data store 220 is part of the data collection system 150.

Each of the images and/or videos recorded in the data store 220 for training the machine learning models 230 can be defined as a base image and can be associated with other data that characterizes an associated procedure and/or rendering specifications. For example, the other data can identify a type of procedure, a location of a procedure, one or more people involved in performing the procedure, surgical objectives, and/or an outcome of the procedure. Alternatively, or in addition, the other data can indicate a stage of the procedure with which the image or video corresponds, rendering specification with which the image or video corresponds and/or a type of imaging device that captured the image or video (e.g., and/or, if the device is a wearable device, a role of a particular person wearing the device, etc.). Further, the other data can include image-segmentation data that identifies and/or characterizes one or more objects (e.g., tools, anatomical objects, etc.) that are depicted in the image or video. The characterization can indicate the position, orientation, or pose of the object in the image. For example, the characterization can indicate a set of pixels that correspond to the object and/or a state of the object resulting from a past or current user handling. Localization can be performed using a variety of techniques for identifying objects in one or more coordinate systems.

The machine learning training system 225 uses the recorded data in the data store 220, which can include the simulated surgical data (e.g., set of virtual images) and actual surgical data to train the machine learning models 230. The machine learning model 230 can be defined based on a type of model and a set of hyperparameters (e.g., defined based on input from a client device). The machine learning models 230 can be configured based on a set of parameters that can be dynamically defined based on (e.g., continuous or repeated) training (i.e., learning, parameter tuning). Machine learning training system 225 can use one or more optimization algorithms to define the set of parameters to minimize or maximize one or more loss functions. The set of (learned) parameters can be stored as part of a trained machine learning model 230 using a specific data structure for that trained machine learning model 230. The data structure can also include one or more non-learnable variables (e.g., hyperparameters and/or model definitions).

Machine learning execution system 240 can access the data structure(s) of the machine learning models 230 and accordingly configure the machine learning models 230 for inference (i.e., prediction). The machine learning models 230 can include, for example, a fully convolutional network adaptation, an adversarial network model, an encoder, a decoder, or other types of machine learning models. The type of the machine learning models 230 can be indicated in the corresponding data structures. The machine learning model 230 can be configured in accordance with one or more hyperparameters and the set of learned parameters.

The machine learning models 230, during execution, receive, as input, surgical data to be processed and subsequently generate one or more inferences according to the training. For example, the video data captured by the video recording system 104 can include data streams (e.g., an array of intensity, depth, and/or RGB values) for a single image or for each of a set of frames (e.g., including multiple images or an image with sequencing data) representing a temporal window of fixed or variable length in a video. The video data that is captured by the video recording system 104 can be received by the data reception system 205, which can include one or more devices located within an operating room where the surgical procedure is being performed. Alternatively, the data reception system 205 can include devices that are located remotely, to which the captured video data is streamed live during the performance of the surgical procedure. Alternatively, or in addition, the data reception system 205 accesses the data in an offline manner from the data collection system 150 or from any other data source (e.g., local or remote storage device).

The data reception system 205 can process the video data received. The processing can include decoding and/or decompression when a video stream is received in an encoded or compressed format such that data for a sequence of images can be extracted and processed. The data reception system 205 can also process other types of data included in the input surgical data. For example, the surgical data, as part of the device data, can include additional non-video data streams, such as audio data, RFID data, textual data, measurements from one or more surgical instruments/sensors, etc., that can represent stimuli/procedural states from the operating room. The data reception system 205 synchronizes the different inputs from the different devices/sensors before inputting them in the machine learning processing system 210.

The machine learning models 230, once trained, can analyze the input surgical data, and in one or more aspects, predict and/or characterize structures included in the video data included in the surgical data. The video data can include sequential images and/or encoded video data (e.g., using digital video file/stream formats and/or codecs and containers, such as MP4, H.264, MOV, WEBM, AVCHD, OGG, etc.). The prediction and/or characterization of the structures can include segmenting the video data or predicting the localization of the structures with a probabilistic heatmap. In some instances, the one or more machine learning models include or are associated with a preprocessing or augmentation (e.g., intensity normalization, resizing, cropping, etc.) that is performed prior to segmenting the video data. An output of the one or more machine learning models can include image-segmentation or probabilistic heatmap data that indicates which (if any) of a defined set of structures are predicted within the video data, a location and/or position and/or pose of the structure(s) within the video data, and/or state of the structure(s). The location can be a set of coordinates in an image/frame in the video data. For example, the coordinates can provide a bounding box. The coordinates can provide boundaries that surround the structure(s) being predicted. The machine learning models 230, in one or more examples, are trained to perform higher-level predictions and tracking, such as predicting a phase of a surgical procedure and tracking one or more surgical instruments used in the surgical procedure.

While some techniques for predicting a surgical maneuver in the surgical procedure are described herein, it should be understood that any other technique for maneuver prediction can be used without affecting the aspects of the technical solutions described herein. In some examples, the machine learning processing system 210 includes a maneuver detector 250 that uses the machine learning models to identify maneuvers within the surgical procedure ("procedure"). Maneuver detector 250 uses a particular procedural tracking data structure 255 from a list of procedural tracking data structures. Maneuver detector 250 selects the procedural tracking data structure 255 based on the type of surgical procedure that is being performed. In one or more examples, the type of surgical procedure is predetermined or input by actor 112. The procedural tracking data structure 255 identifies a set of potential maneuvers that can correspond to a part of the specific type of procedure.

In some examples, the procedural tracking data structure 255 can be a graph that includes a set of nodes and a set of edges, with each node corresponding to a potential maneuver. The edges can provide directional connections between nodes that indicate (via the direction) an expected order during which the maneuvers will be encountered throughout an iteration of the procedure. The procedural tracking data structure 255 may include one or more branching nodes that feed to multiple next nodes and/or can include one or more points of divergence and/or convergence between the nodes. In some instances, a maneuver indicates a procedural action (e.g., surgical action) that is being performed or has been performed and/or indicates a combination of actions that have been performed. In some instances, a maneuver relates to a biological state of a patient undergoing a surgical procedure. For example, the biological state can indicate a complication (e.g., blood clots, clogged arteries/veins, etc.), pre-condition (e.g., lesions, polyps, etc.). In some examples, the machine learning models 230 are trained to detect an "abnormal event," such as hemorrhaging, arrhythmias, blood vessel abnormality, etc. In some aspects, an "abnormal event" is an adverse event that occurs during the surgical procedure, such as bleeding, leaks, direct maneuver in critical structure, etc. In some aspects, the abnormal event can also include start/end of a new surgical maneuver. Further, in some aspects, the abnormal event can include the detection of a new surgical instrument entering the view of the camera.

Each node within the procedural tracking data structure 255 can identify one or more characteristics of the maneuver corresponding to that node. The characteristics can include visual characteristics. In some instances, the node identifies one or more tools that are typically in use or availed for use (e.g., on a tool tray) during the maneuver. The node also identifies one or more roles of people who are typically performing a surgical task, a typical type of movement (e.g., of a hand or tool), etc. Thus, maneuver detector 250 can use the segmented data generated by model execution system 240 that indicates the presence and/or characteristics of particular objects within a field of view to identify an estimated node to which the real image data corresponds. Identification of the node (i.e., maneuver) can further be based upon previously detected maneuvers for a given procedural iteration and/or other detected input (e.g., verbal audio data that includes person-to-person requests or comments, explicit identifications of a current or past maneuver, information requests, etc.).

The maneuver detector 250 outputs the maneuver prediction associated with a portion of the video data that is analyzed by the machine learning processing system 210. The maneuver prediction is associated with the portion of the video data by identifying a start time and an end time of the portion of the video that is analyzed by the machine learning execution system 240. The maneuver prediction that is output can include an identity of a surgical maneuver as detected by the maneuver detector 250 based on the output of the machine learning execution system 240. Further, the maneuver prediction, in one or more examples, can include identities of the structures (e.g., instrument, anatomy, etc.) that are identified by the machine learning execution system 240 in the portion of the video that is analyzed. The maneuver prediction can also include a confidence score of the prediction. Other examples can include various other types of information in the maneuver prediction that is output.

Figure 3:
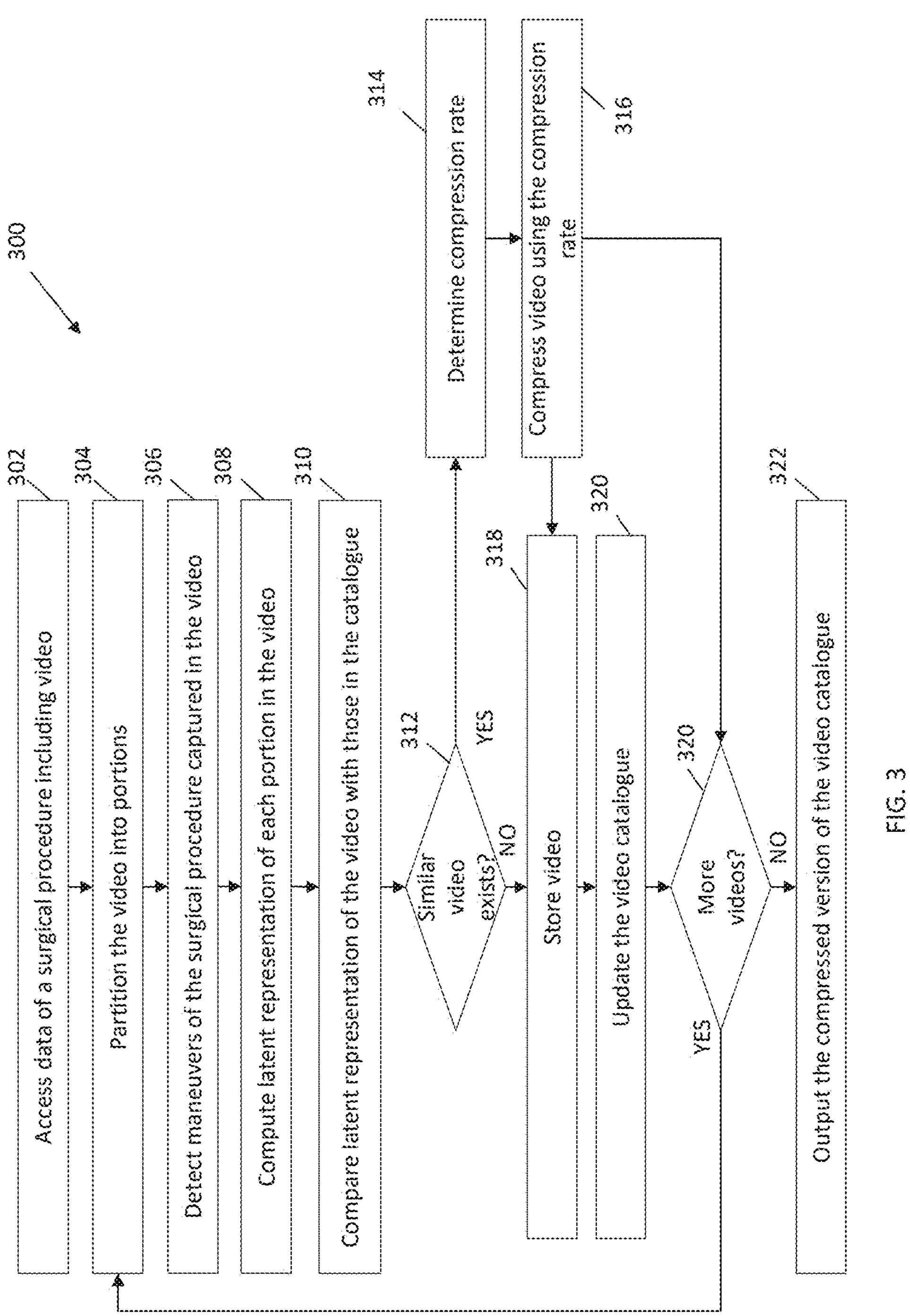
FIG. 3 depicts a flowchart of a method for cataloguing a video in a surgical video catalogue according to one or more aspects.

FIG. 3 depicts a flowchart of a method for compressing a catalogue of surgical video according to one or more aspects.

Method 300 is a computer-implemented method that can be executed by system 100 of FIG. 1. Method 300 includes using the machine learning processing system 210 to detect, predict, and track features, including surgical maneuvers, anatomical structures, and instruments, in a video of a surgical procedure. System 100 processes different portions of the video being analyzed differently based on the maneuver prediction for each portion, and existing videos in a video catalogue (402). The maneuver prediction is output by the machine learning processing system 210. Based on the analysis of the different portions of a video, and the existing data in the other videos, similar videos can be determined, and the video catalogue (402) can be compressed by compressing similar videos. In one or more aspects, the compression rate to be used to compress a video is determined based on the video's similarity with one or more existing videos in the video catalogue (402).

At block 302, system 100 can access input data, including, for example, video data, spatial data, and sensor data temporally associated with a video (file/stream) of a surgical procedure. It should be understood that the sequence of operations depicted in FIG. 3 is exemplary, and that the depicted operations can be performed in a different order, or in parallel in some aspects. The input data can be accessed in an offline manner (post-surgery), for example, from the data collection system 150. Alternatively, or in addition, the input data is accessed in real-time. In one or more examples, accessing the input data includes receiving or accessing one or more portions of the video of a surgical procedure. In some examples, the video is transmitted to the data reception system 205 as a video stream in real-time as the surgical procedure is being performed. This transmission may occur using any variety of video compression and container technology and streaming protocols (e.g., HTTP, RTMP, etc.). The data reception system 205 stores the video for the processing by the method 300 prior to updating the video catalogue (402).

Figure 4:
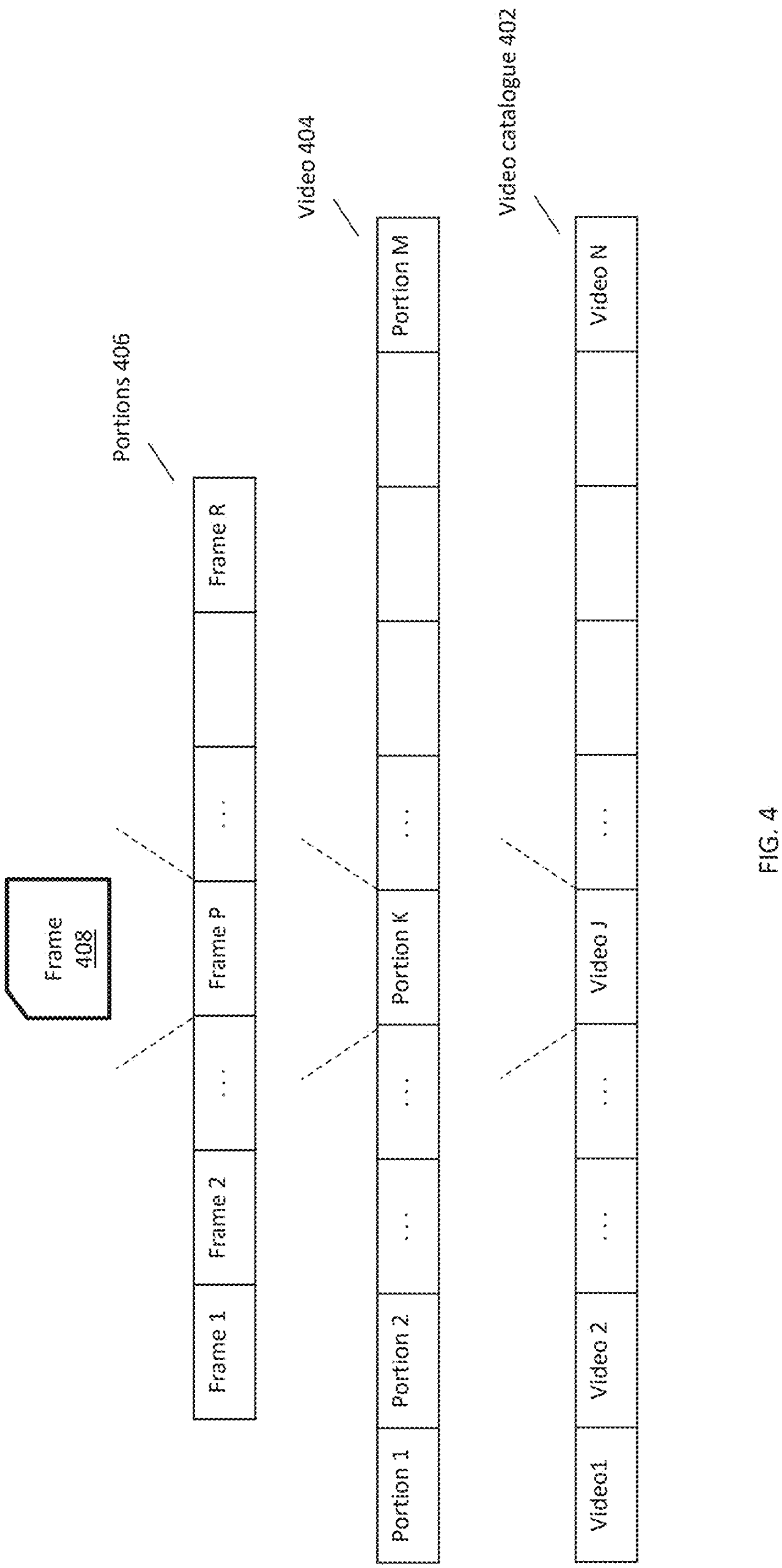
FIG. 4 depicts a video catalogue being analyzed for feature contingent surgical video compression according to one or more aspects.

FIG. 4 depicts a video catalogue being analyzed for feature contingent surgical video compression according to one or more aspects. It is understood that the depiction is an exemplary scenario and that video catalogues can be analyzed for compression in a different manner using the technical solutions described herein. The data collection system 150 can store the captured videos from several surgical procedures in a video catalogue 402. The video catalogue 402 can store several videos 404. Each video 404 includes multiple portions 406 (or segments), where each portion 406 includes one or more frames 408.

The video catalogue 402 can be a database in one or more examples. The video catalogue 402 can use any database management architecture that is known or will be developed later. The videos 404 can be stored using one or more electronic files, such as AVI files, MP4 files, MOV files, etc. The frames 408 in each video 404 can be encoded based on the format and/or codec used to store that video 404. Here, a "frame" 406 can be an image that is part of a sequence of images that are played back at the desired rate, for example, 30 frames per second, 60 frames per second, etc. so that the sequence of images is viewed as a motion picture, i.e., "video."

In one or more aspects, the video catalogue 402 can be the entire collection of videos in the data collection system 150. In some aspects, the video catalogue 402 includes a group of videos stored in the data collection system 150. For example, the video catalogue 402 can represent videos of surgical procedures performed at a particular hospital/institution, surgical procedures performed by particular surgeon/medical personnel, surgical procedures of a particular type, surgical procedures performed over a particular duration (one year, two years, one month, one quarter, etc.). Further, in some examples, the video catalogue 402 can include videos captured using particular equipment (e.g., specific type of camera 108). In one or more aspects, the video catalogue 402 can include videos of the same surgical procedure captured using different cameras 108.

Referring to the flowchart in FIG. 3, at block 304, the machine learning processing system 210 splits the video 404 that is being analyzed into one or more portions 406. A portion 406 can be a set of frames that are played back during a predetermined duration of the video 404 (e.g., from starting timepoint 30 seconds to an ending timepoint 42 seconds). In other examples, portion 406 is a predetermined number of frames 408.

The portions 406 in video 404 are selected in a sequential manner in some examples. For example, if a portion is predetermined to be five frames, the first portion 406 with frame #1-5 is analyzed, subsequently the second portion 406 including frame #6-10, and so on until all of the frames 408 in the video 404 are analyzed.

In other examples, portions 406 in the video 404 can be operated in parallel. For example, the first portion, the second portion, and the third portion can be analyzed in parallel. It is understood that any number of portions 406 can be analyzed in parallel and that the above is just one example.

At block 306, the machine learning execution system 240 uses the trained machine learning models 230 to detect one or more maneuvers of the surgical procedure, at block 306. In one or more aspects, each portion 406 is analyzed (sequentially or in parallel) to detect a maneuver being performed in that portion 406. Alternatively, in one or more aspects, the partitioning of the video 404 into portions 406 can be performed after the machine learning execution system 240 detects the maneuvers in the surgical procedure. In other words, each of the portion 406 represents a video-clip or segment that depicts a particular maneuver being performed in the surgical procedure.

The machine learning execution system 240 generates a latent representation of each portion 406 of the video 404, at block 308.

Figure 5:
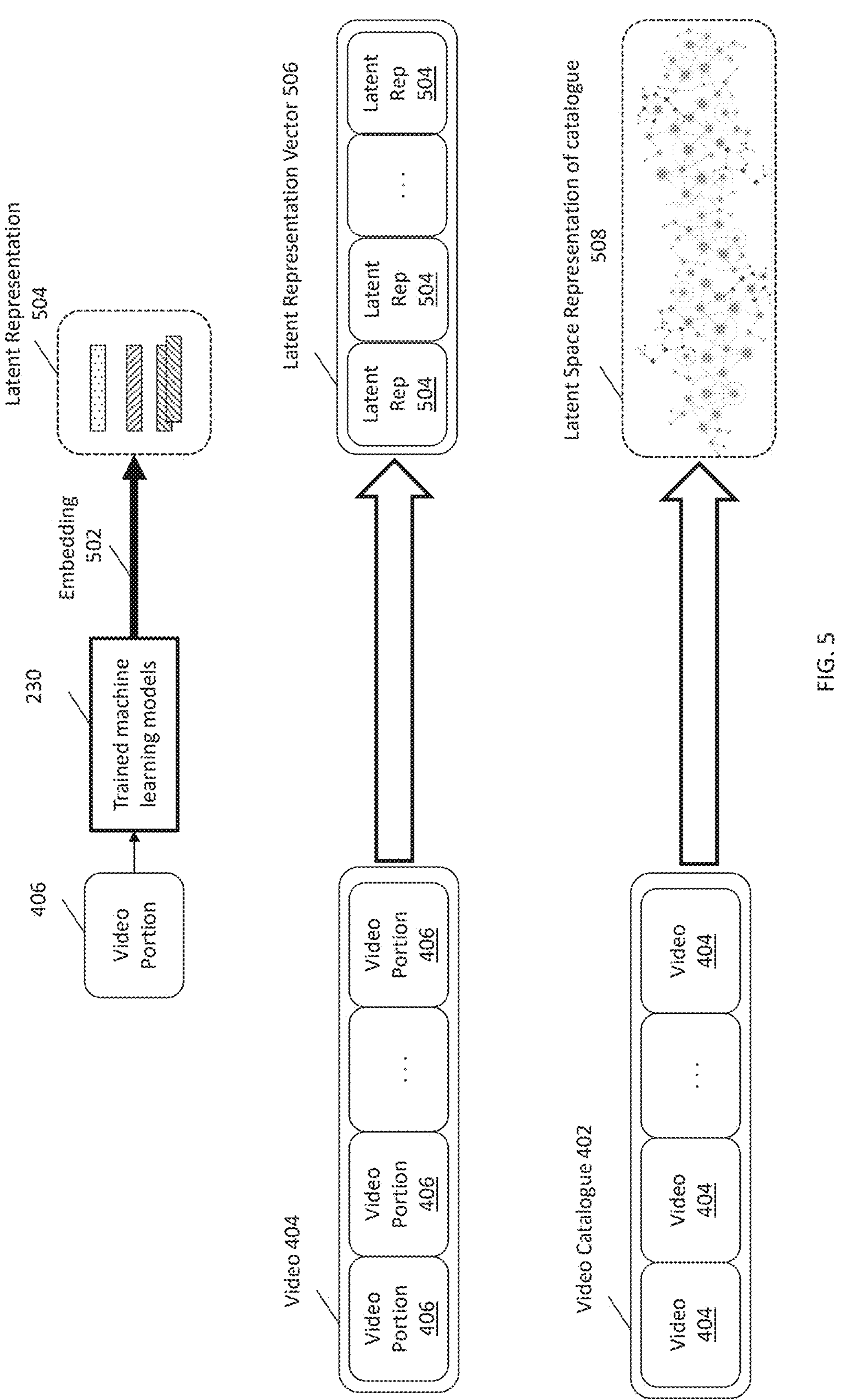
FIG. 5 depicts a block diagram of latent representation of the videos according to one or more aspects.

FIG. 5 depicts a block diagram of latent representation of the videos according to one or more aspects. When a video portion 406 is analyzed by the trained machine learning models 230, a latent representation 504 of the video portion 406 is generated. The latent representation 504 is a lower-dimensional representation of the portion 406, and can include vector representation of the portion 406. The latent representation 504 is based on the weight values, and other hyper parameters of the trained machine learning models 230. An embedding 502 can map the video portion 406 to a corresponding latent representation 504. In one or more aspects, the trained machine learning models 230 can include an encoder machine learning model that generates the latent representation 504. The trained machine learning models 230 encode spatial-temporal video information from the portion 406 into the latent representation 504. In addition to the portion 406, the latent representation 504 can also be based on the other data stored in the surgical data. For example, the device information (e.g., energy information, instrument information, etc.) and surgical procedure metadata can be used to generate the latent representation 504.

A collection of the latent representations 504 of the several portions 406 in each video 404 of the video catalogue 402 is referred to as a latent representation space 508. The latent representation space 508 is, in one or more aspects, a vector space in which a point represents a particular latent representation 504 and consequently a video portion 406. The latent representation space 508 is stored by the data collection system 150.

Accordingly, by computing the latent representations 504 for each portion 406 in the video 404, the video 404 can be represented as a vector of latent representations 504, <L1, L2, . . . . Ln>, where Li represents the latent representation 504 of the $i^{th}$ video portion 406 in the video 404.

At block 310, the vector of latent representations of the video 404 is compared with the latent representations of existing videos 404 in the catalogue 402. In one or more aspects, the comparison is limited to a selected number of videos from the video catalogue 402 to prevent the comparison from requiring excessive computing resources and/or time based on the size and number of videos in the video catalogue 402. The selected number of videos 404 from the video catalogue 402 can be selected based on existing videos 404 having the same maneuvers as the video 404 being analyzed. Alternatively, or in addition, existing videos 404 with the same maneuvers and in the same sequence may be selected. Alternatively, or in addition, the selection of the existing videos can be performed based on videos from same hospital, same surgeon/staff, same equipment, same patient, same surgical procedure, same outcome, etc.

At block 312, the comparison facilitates determining whether another similar video 404 exists in the video catalogue 402. The comparison of the latent representations 504 is more efficient compared to comparison of the video portions 406 (in the video formatting).

The comparison includes computing distances between the corresponding latent representations 504 from two videos 404 being compared. In one or more aspects, the "corresponding latent representations 504" from two videos 404 are latent representations 504 that represent the same maneuver. For example, consider that in video-1, L1 represents a first portion 406 in which a dissection is performed, L2 represents a second portion 406 in which an incision is performed, and L3 represents a third portion in which a suturing is performed. Further, consider that in video-2, LR1 represents a first portion 406 in which a dissection is performed, LR2 represents a second portion in which a debridement is performed, LR3 represents a third portion 406 in which an incision is performed, LR4 represents a fourth portion 406 in which another debridement is performed, and LR5 represents a fifth portion 406 in which a suturing is performed. Here, the comparison between video-1 and video-2 includes computing distances between the pairs <L1, LR1>, <L2, LR3>, and <L3, LR5>.

In one or more aspects, computing the similarity can include computing a similarity score based on the distances computed. For example, an average, a weighted average, median, or any other statistical technique can be used.

In addition, if there are any portions 406 that are not used for the similarity comparison (e.g., LR2 and LR4 in above scenario), such portions 406 can be used to adjust the similarity score. In some examples, the adjustment can be based on the type of the maneuver represented by the portion 406. For example, a first type of maneuver (e.g., debridement) may be assigned a first adjustment factor, and a second type of maneuver (e.g., bleeding) may be assigned a second adjustment factor. The adjustment factors may be assigned based on several factors, such as effect of the maneuver on the surgical procedure, how common the maneuver is performed by surgeons, etc. The adjustment factor may be added, subtracted, multiplied, etc., to/from the similarity score based on the computed distances.

A first video 404 is deemed to be similar to a second video 404 if the similarity score between the two latent representations is within a predetermined range. The predetermined range can be a configurable value.

If a second video 404 is identified in the video catalogue 402 that is similar to the first video 404 being analyzed based on a comparison of the respective latent representations 504, a compression rate for the first video 404 is determined, at block 314. For example, if the similarity score is high (or low), which represents that the first video 404 is substantially identical to the second video 404 that exists in the video catalogue 402, a higher compression rate is used to store the first video 404.

The compression rate can be adjusted (higher/lower) by selecting the compression protocol (e.g., codec) being used to compress the first video 404, in one or more aspects. Alternatively, or in addition, the compression rate can be adjusted by configuring one or more parameters being used to store the first video 404 using the compression protocol. In one or more aspects, the compression rate can be adjusted by adjusting a bit rate (e.g., bits per second) of the first video 404 being stored. Alternatively, or in addition, the compression rate can be adjusted by configuring parameters such as image size, frame rate, amount of movement between frames, etc. It is understood that other factors may be adjusted to adjust the compression rate in other examples.

Further, at block 316, the first video 404 is compressed using the determined compression rate. The compressed video is stored in the video catalogue 402, at block 318. The video catalogue 402 is updated, at block 320. In one or more aspects, the video catalogue is updated to link the first video 404 with the second video 404. The link indicates the similarity score in one or more aspects. In some aspects, when the first video 404 is compared with the existing videos in the video catalogue 402 (e.g., selected existing videos), a link is created for each pair, with the link representing the similarity score. The "link" can be created by storing metadata for the first video in the video catalogue 402, in a header of the first video 404, etc. For example, the metadata can include identifiers of the first video 404 and the second video 404 that is compared with the first video 404, and the similarity score of the two videos.

Further, updating the video catalogue 402 includes storing the high-fidelity version of the first video 404 (uncompressed) in an archive, and storing a link to the high-fidelity version in the metadata. The link can be a uniform resource link (URL), a hash, or any other type of identifier of the archived high-fidelity version of the first video 404. The archived versions can be stored as part of the data collection system 150, or a separate remote storage (not shown).

By compressing the first video at a higher compression rate (compared to default case in block 318), the amount of storage required to store the first video 404 in the video catalogue 402 is reduced.

In one or more aspects, when a similar existing video 404 is identified from the video catalogue 402, a user/operator is prompted whether to compress the first video 404 being analyzed with the higher compression rate (at block 314). Only if the operator selects to proceed with such a higher compression rate, the compression is performed and the compressed first video stored in the video catalogue (at 316). In this manner, the operator can determine if an abnormal event, such as bleeding, leaking, etc. occurred in the particular video portion 406, or if the video portion 406 is associated with such an abnormal event that may occur later in the video 404 (in the case of post-surgery analysis of the video).

Alternatively, if it is deemed that the first video 404 is not similar to any existing video 404 from the video catalogue 402 the first video 404 is stored with a default compression rate, at block 318. The default compression rate can be a lower compression, to store the first video at the highest possible fidelity.

Further, the video catalogue 402 is updated, at block 320. The update includes storing the latent representations 504 of the first video 404 in the latent representation space 508.

At block 320, a determination is made if additional videos 404 are to be analyzed. If additional videos 404 exist, method 300 is repeated by partitioning the next video 404 (at 304). As noted earlier, multiple videos 404 can be selected for parallelized analysis and compression.

In one or more aspects, the video catalogue 402 can be repeatedly compressed using method 300 by analyzing each video in the video catalogue 402 by comparing it with the video catalogue 402 itself. Such an exercise may be performed at a predetermined frequency so that the video catalogue 402 is updated to compress similar videos 404. In some aspects, during such iterations, only the videos 404 that are not compressed in a previous iteration are compared.

Once all the videos are analyzed, the compressed video catalogue 402 can be output in its entirety, at block 322. In this manner, the video catalogue can be compressed using the technical solutions described herein.

The storing of a video 404 can include transmitting the compressed video to a remote location over a communication network.

Figure 6:
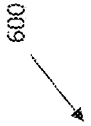
FIG. 6 depicts a flowchart of a method for reconstructing a video using a compressed video according to one or more aspects.
Figure 6:
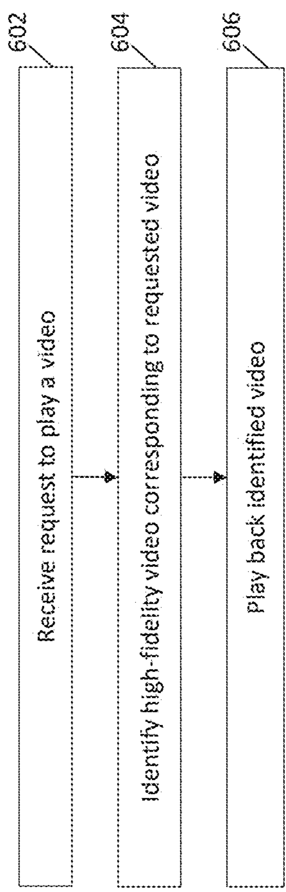

FIG. 6 depicts a flowchart of a method for playing back a video stored in a compressed video catalogue according to one or more aspects. The method 600 includes receiving a request to playback a video 404 from the video catalogue, at block 602. A high-fidelity video corresponding to the request is identified, at block 604. For example, if the requested video 404 is stored in high-fidelity (i.e., without compression), the video 404 stored in the video catalogue 402 is played back, at block 606. Alternatively, if the requested video is stored with a higher compression rate, in one or more aspects, the operator/user/requestor is notified that a lower-fidelity video is stored in the video catalogue 402, and asked if s/he prefers to playback the lower-fidelity video 404. Based on the operator's response to playback the lower-fidelity video, the stored video 404 is played back, at block 606.

Alternatively, the operator can request to playback the corresponding high-fidelity video 404 that is archived. The archived video can be identified using the stored link in the metadata.

Further yet, in one or more aspects, the operator is given an option to playback the similar video in the video catalogue that is stored at high-fidelity (second video 404 in method 300). In some aspects, the operator is shown the similarity score(s) of the requested video with other high-fidelity videos in the video catalogue 402. The similarity scores can be displayed from the metadata. The operator can subsequently identify the high-fidelity video s/he would like to playback instead of the low-fidelity video. The identified video is played back, at block 606.

Aspects of the technical solutions described herein can improve CAS systems, particularly by facilitating video storage optimization. Optimized/selective compression described herein improves (i.e., reduces) storage requirements. Aspects of the technical solutions described herein can also improve video transmission. The optimized/selective compression can be used to improve (i.e., reduce) network bandwidth requirements. The technical solutions described herein use automatic analytics generation (optimal video compression, i.e., no image information is retained, just relevant metadata). Further, the technical solutions described herein facilitate improvements to computing technology, particularly computing techniques used for video storage and transmission.

Aspects of the technical solutions described herein facilitate one or more machine learning models, such as computer vision models, to process images obtained from a video of the surgical procedure using spatial-temporal information. The machine learning models using techniques such as neural networks to use information from the video and (if available) robotic sensor platform to predict one or more features, such as anatomical structures, surgical instruments, in an input window of the live video feed, and further refine the predictions using additional machine learning models that can predict a maneuver of the surgical procedure. The machine learning models can be trained to identify the surgical maneuver(s) of the procedure and structures in the field of view by learning from raw image data. When in a robotic procedure, the computer vision models can also accept sensor information (e.g., instruments enabled, mounted, etc.) to improve the predictions. Computer vision models that predict instruments and critical anatomical structures use temporal information from the maneuver prediction models to improve the confidence of the predictions in real-time or in an offline manner.

The predictions and the corresponding confidence scores can be used to generate and display video based on video captured during a surgical procedure. The generated video is a compressed version of the captured video data, where the compression is performed in a feature contingent manner across a catalogue of videos. Aspects of the technical solutions described herein provide a practical application in surgical procedures and storage of large amounts of data (Terabytes, Petabytes, etc.) captured during surgical procedures.

It should be noted that although some of the drawings depict endoscopic videos being analyzed, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

It should be noted that while aspects of the technical solutions are described herein using surgical video as examples, the technical solutions described herein are applicable to other technical fields where video data storage is a technical challenge. For example, social media, security camera data storage, video-logging servers, media servers, etc., can use the technical solutions herein to reduce data storage requirements and thus, improve one or more systems.

Technical solutions described herein provide a practical application to a technical challenge rooted in computing technology, particularly data storage. Technical solutions described herein convert the video data from one storage format to another, uncompressed to compressed, and vice versa.

Figure 7:
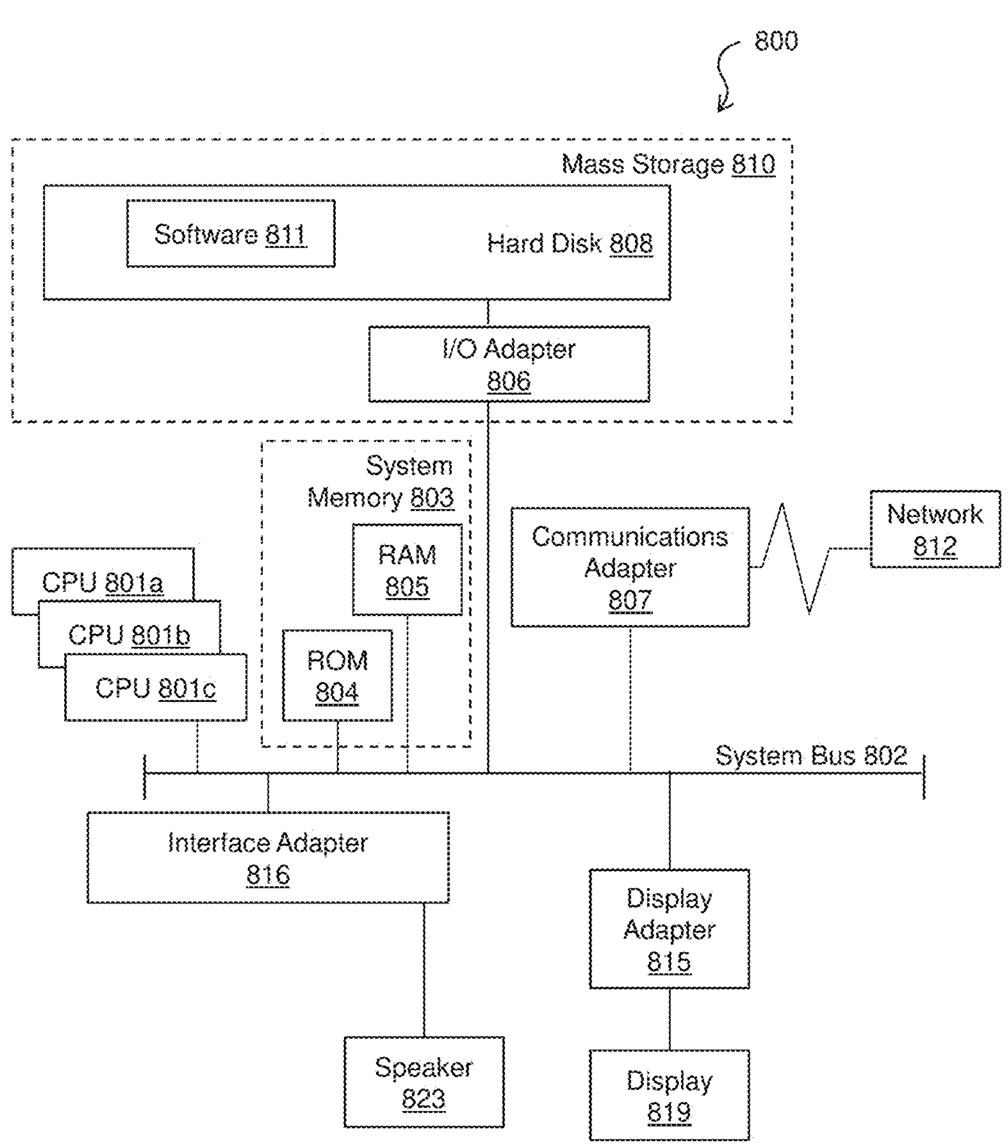
FIG. 7 depicts a computer system in accordance with one or more aspects.

Turning now to FIG. 7, a computer system 800 is generally shown in accordance with an aspect. The computer system 800 can be an electronic computer framework comprising and/or employing any number and combination of computing devices and networks utilizing various communication technologies, as described herein. The computer system 800 can be easily scalable, extensible, and modular, with the ability to change to different services or reconfigure some features independently of others. The computer system 800 may be, for example, a server, desktop computer, laptop computer, tablet computer, or smartphone. In some examples, computer system 800 may be a cloud computing node. Computer system 800 may be described in the general context of computer-executable instructions, such as program modules, being executed by a computer system. Generally, program modules may include routines, programs, objects, components, logic, data structures, and so on that perform particular tasks or implement particular abstract data types. Computer system 800 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 7, the computer system 800 has one or more central processing units (CPU(s)) 801*a*, 801*b*, 801*c*, etc. (collectively or generically referred to as processor(s) 801). The processors 801 can be a single-core processor, multi-core processor, computing cluster, or any number of other configurations. The processors 801, also referred to as processing circuits, are coupled via a system bus 802 to a system memory 803 and various other components. The system memory 803 can include one or more memory devices, such as read-only memory (ROM) 804 and a random access memory (RAM) 805. The ROM 804 is coupled to the system bus 802 and may include a basic input/output system (BIOS), which controls certain basic functions of the computer system 800. The RAM is read-write memory coupled to the system bus 802 for use by the processors 801. The system memory 803 provides temporary memory space for operations of said instructions during operation. The system memory 803 can include graphics memory, random access memory (RAM), read-only memory, flash memory, or any other suitable memory systems.

The computer system 800 comprises an input/output (I/O) adapter 806 and a communications adapter 807 coupled to the system bus 802. The I/O adapter 806 may be a small computer system interface (SCSI) adapter that communicates with a hard disk 808 and/or any other similar component. The I/O adapter 806 and the hard disk 808 are collectively referred to herein as a mass storage 810.

Software 811 for execution on the computer system 800 may be stored in the mass storage 810. The mass storage 810 is an example of a tangible storage medium readable by the processors 801, where the software 811 is stored as instructions for execution by the processors 801 to cause the computer system 800 to operate, such as is described hereinbelow with respect to the various Figures. Examples of computer program product and the execution of such instruction is discussed herein in more detail. The communications adapter 807 interconnects the system bus 802 with a network 812, which may be an outside network, enabling the computer system 800 to communicate with other such systems. In one aspect, a portion of the system memory 803 and the mass storage 810 collectively store an operating system, which may be any appropriate operating system to coordinate the functions of the various components shown in FIG. 7.

Additional input/output devices are shown as connected to the system bus 802 via a display adapter 815 and an interface adapter 816 and. In one aspect, the adapters 806, 807, 815, and 816 may be connected to one or more I/O buses that are connected to the system bus 802 via an intermediate bus bridge (not shown). A display 819 (e.g., a screen or a display monitor) is connected to the system bus 802 by a display adapter 815, which may include a graphics controller to improve the performance of graphics-intensive applications and a video controller. A keyboard, a mouse, a touchscreen, one or more buttons, a speaker, etc., can be interconnected to the system bus 802 via the interface adapter 816, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI), or PCI express. Thus, as configured in FIG. 7, the computer system 800 includes processing capability in the form of the processors 801, and, storage capability including the system memory 803 and the mass storage 810, input means such as the buttons, touchscreen, and output capability including the speaker 823 and the display 819.

In some aspects, the communications adapter 807 can transmit data using any suitable interface or protocol, such as the internet small computer system interface, among others. The network 812 may be a cellular network, a radio network, a wide area network (WAN), a local area network (LAN), or the Internet, among others. An external computing device may connect to the computer system 800 through the network 812. In some examples, an external computing device may be an external web server or a cloud computing node.

It is to be understood that the block diagram of FIG. 7 is not intended to indicate that the computer system 800 is to include all of the components shown in FIG. 7. Rather, the computer system 800 can include any appropriate fewer or additional components not illustrated in FIG. 7 (e.g., additional memory components, embedded controllers, modules, additional network interfaces, etc.). Further, the aspects described herein with respect to computer system 800 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects.

Figure 8:
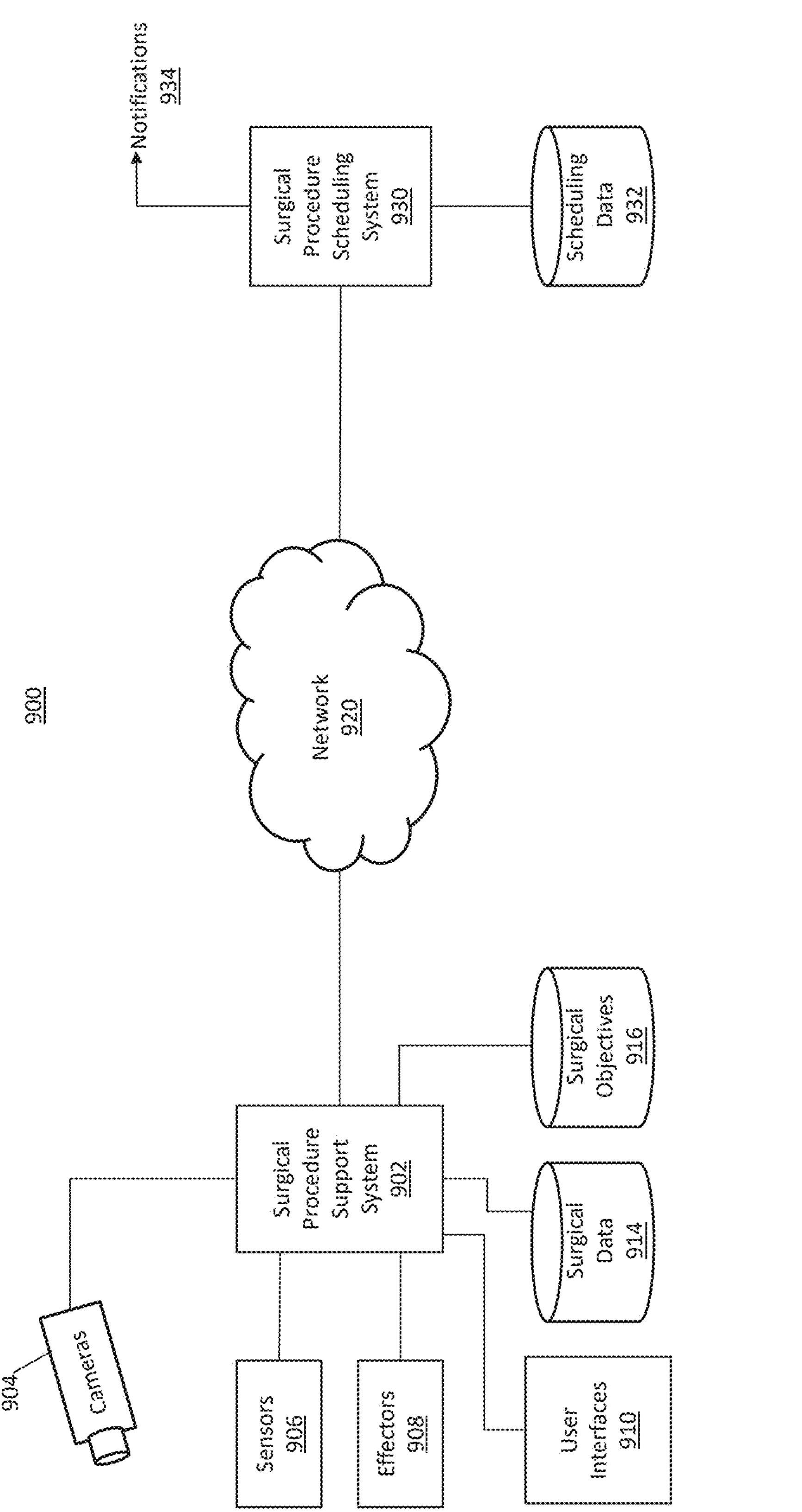
FIG. 8 depicts a surgical procedure system in accordance with one or more aspects.

FIG. 8 depicts a surgical procedure system 900 in accordance with one or more aspects. The example of FIG. 8 depicts a surgical procedure support system 902 configured to communicate with a surgical procedure scheduling system 930 through a network 920. The surgical procedure support system 902 can include or may be coupled to the system 100 of FIG. 1. The surgical procedure support system 902 can acquire image data, such as images 302 of FIG. 3, using one or more cameras 904. The surgical procedure support system 902 can also interface with a plurality of sensors 906 and effectors 908. The sensors 906 may be associated with surgical support equipment and/or patient monitoring. The effectors 908 can be robotic components or other equipment controllable through the surgical procedure support system 902. The surgical procedure support system 902 can also interact with one or more user interfaces 910, such as various input and/or output devices. The surgical procedure support system 902 can store, access, and/or update surgical data 914 associated with a training dataset and/or live data as a surgical procedure is being performed. The surgical procedure support system 902 can store, access, and/or update surgical objectives 916 to assist in training and guidance for one or more surgical procedures.

The surgical procedure scheduling system 930 can access and/or modify scheduling data 932 used to track planned surgical procedures. The scheduling data 932 can be used to schedule physical resources and/or human resources to perform planned surgical procedures. Based on the surgical maneuver as predicted by the one or more machine learning models 230 and a current operational time, the surgical procedure support system 902 can estimate an expected time for the end of the surgical procedure. This can be based on previously observed similarly complex cases with records in the surgical data 914. A change in a predicted end of the surgical procedure can be used to inform the surgical procedure scheduling system 930 to prepare the next patient, which may be identified in a record of the scheduling data 932. The surgical procedure support system 902 can send an alert to the surgical procedure scheduling system 930 that triggers a scheduling update associated with a later surgical procedure. The change in scheduling can be captured in the scheduling data 932. Predicting an end time of the surgical procedure can increase efficiency in operating rooms that run parallel sessions, as resources can be distributed between the operating rooms. Requests to be in an operating room can be transmitted as one or more notifications 934 based on the scheduling data 932 and the predicted surgical maneuver.

As surgical maneuvers and steps are completed, progress can be tracked in the surgical data 914 and status can be displayed through the user interfaces 910. Status information may also be reported to other systems through the notifications 934 as surgical maneuvers are completed or if any issues are observed, such as complications.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the “C” programming language or similar programming languages. The computer-readable program instructions may execute entirely on the user’s computer, partly on the user’s computer, as a stand-alone software package, partly on the user’s computer and partly on a remote computer, or entirely on the remote computer or server. In the latter scenario, the remote computer may be connected to the user’s computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms “comprises,” “comprising,” “includes,” “including,” “has,” “having,” “contains,” or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A computer-implemented method comprising:

segmenting, by a processor, a first video of a surgical procedure into a sequence of video portions;

generating, by the processor, a first sequence of latent representations corresponding to the sequence of video portions in the first video using an encoder machine learning model;

computing, by the processor, a similarity score of the first video and a second video from a video catalogue that comprises a plurality of videos, including the second video, the computing based on the first sequence of latent representations and a second sequence of latent representations of the second video;

determining, by the processor, a compression rate for the first video based on the similarity score;

generating, by the processor, a compressed first video by compressing the first video using the compression rate that is determined; and storing, by the processor, the compressed first video in the video catalogue.

2. The computer-implemented method of claim 1, wherein the first video is stored in an archive, and the video catalogue is updated to store a link between the compressed first video and the first video in the archive.

3. The computer-implemented method of claim 1, wherein the first video is segmented, using one or more machine learning models, into the sequence of video portions, wherein each video portion represents a maneuver in the surgical procedure.

4. The computer-implemented method of claim 1, wherein the first video is captured using a camera that is one from a group comprising an endoscopic camera, a portable camera, and a stationary camera.

5. The computer-implemented method of claim 1, wherein the second video is stored using a first compression rate, the first compression rate providing high-fidelity, and based on the similarity score being within a predetermined range, using a second compression rate for the first video, the second compression rate providing a lower fidelity than the second video.

6. The computer-implemented method of claim 5, wherein the second video is of the same surgical procedure as the first video.

7. The computer-implemented method of claim 5, wherein the second video is of a different surgical procedure than the first video.

8. The computer-implemented method of claim 1, wherein the first video and the second video capture respective surgical procedures, and the second video is selected to be compared with the first video based on one or more attributes selected from a group of attributes comprising type of the surgical procedure, institution of the surgical procedure, staff performing the surgical procedure, equipment used for the surgical procedure, patient of the surgical procedure, and camera used to capture the first video.

9. The computer-implemented method of claim 2, further comprising:

in response to receiving, from a user, a request to playback the first video from the video catalogue, notifying the user of the compressed first video, the first video from the archive, and the second video from the video catalogue.

10. The computer-implemented method of claim 9, wherein the user can select, for playback, one from the compressed first video, the first video from the archive, and the second video from the video catalogue.

11. A system comprising:

a machine learning system comprising one or more machine learning models that are trained to encode a portion of video into a latent representation; and a data collection system configured to generate a compressed copy of a video catalogue that comprises a plurality of videos, each video in the video catalogue comprising a plurality of video portions, wherein generating the compressed copy of the video catalogue comprises:

generating a first sequence of latent representations corresponding to a first sequence of video portions in a first video using the machine learning system;

computing a plurality of similarity scores of the first video with the plurality of videos from the video catalogue, a similarity score between the first video and a second video from the plurality of videos is computed based on the first sequence of latent representations and a second sequence of latent representations of the second video;

based on a determination that the first video is similar to the second video based on the similarity score, generating a compressed first video using a compression protocol that is based on the similarity score; and storing the compressed first video in the video catalogue.

12. The system of claim 11, wherein the plurality of similarity scores is stored in metadata of the video catalogue.

13. The system of claim 11, wherein the plurality of similarity scores is stored in metadata of the compressed first video.

14. The system of claim 11, wherein the first video is archived, and the compressed first video is linked to the first video that is archived.

15. The system of claim 11, wherein, in response to the similarity score being within a first range that indicates that the first video is similar to the second video, adjusting a compression rate to a higher value, and in response to the similarity score being within a second range that indicates that the first video is not similar to the second video, adjusting the compression rate to a lower value.

16. The system of claim 15, wherein adjusting the compression rate comprises adjusting one or more attributes from a group comprising image size, frame rate, amount of movement between frames, bit rate, and codec.

17. A computer program product comprising a memory device having computer-executable instructions stored thereon, which when executed by one or more processors cause the one or more processors to perform a method to catalogue surgical data in a compressed manner, the method comprising:

generating, using a machine learning system, a latent representation space corresponding to a data collection system that stores surgical data for a plurality of surgical procedures, the latent representation space comprising a plurality of latent representations, wherein a latent representation is a vector representation of a portion of surgical data, and wherein each surgical data in the data collection system comprises a plurality of portions; and in response to receiving a first surgical data to be catalogued in the data collection system:

segmenting the first surgical data into a sequence of portions;

generating a first sequence of latent representations corresponding to the sequence of portions in the first surgical data using the machine learning system;

determining, from the latent representation space, a second surgical data that is similar to the first surgical data by comparing the first sequence of latent representations of the first surgical data and a second sequence of latent representations of the second surgical data;

computing a similarity score of the first surgical data and the second surgical data;

determining a first compression rate by adjusting a second compression rate based on the similarity score, the second compression rate is used to store the second surgical data in the data collection system;

generating a compressed first surgical data using the first compression rate; and storing the compressed first surgical data in the data collection system.

18. The computer program product of claim 17, wherein, the first compression rate is higher than the second compression rate.

19. The computer program product of claim 17, wherein storing the compressed first surgical data in the data collection system comprises storing a link between the compressed first surgical data and the second surgical data.

20. The computer program product of claim 17, wherein:

in response to receiving a third surgical data to be catalogued in the data collection system:

segmenting the third surgical data into a third sequence of portions;

generating a third sequence of latent representations corresponding to the third sequence of portions in the third surgical data using the machine learning system;

determining, based on the latent representation space, that the third surgical data is not similar to any of the surgical data in the data collection system;

storing the third surgical data in the data collection system using the second compression rate; and storing the third sequence of latent representations in the latent representation space.

* * * * *